(12) United States Patent
Muecke

(10) Patent No.: US 8,846,382 B2
(45) Date of Patent: Sep. 30, 2014

(54) AIRLIFT BIOREACTOR

(76) Inventor: Oliver Muecke, Basel (CH)

( * ) Notice: Subject to any disclaimer, the term of this patent is extended or adjusted under 35 U.S.C. 154(b) by 736 days.

(21) Appl. No.: 12/375,896

(22) PCT Filed: Jul. 31, 2007

(86) PCT No.: PCT/EP2007/006762

§ 371 (c)(1),
(2), (4) Date: May 27, 2009

(87) PCT Pub. No.: WO2008/014974

PCT Pub. Date: Feb. 7, 2008

(65) Prior Publication Data

US 2009/0303829 A1    Dec. 10, 2009

Related U.S. Application Data

(60) Provisional application No. 60/821,024, filed on Aug. 1, 2006.

(30) Foreign Application Priority Data

Aug. 1, 2006   (IE) .................................. S2006/0571

(51) Int. Cl.
*B01F 13/02*   (2006.01)
*B01F 3/04*    (2006.01)
*C12M 1/00*    (2006.01)
*C12M 1/08*    (2006.01)

(52) U.S. Cl.
CPC .............. *B01F 3/0451* (2013.01); *C12M 23/14* (2013.01); *C12M 29/06* (2013.01); *C12M 29/08* (2013.01); *C12M 27/24* (2013.01)
USPC ......................... 435/295.2; 366/101; 422/227

(58) Field of Classification Search
CPC .... C12M 27/24; C12M 29/08; B01F 3/04517
USPC ......................... 422/227; 366/101, 137, 107; 435/295.1–295.3; 383/3
See application file for complete search history.

(56) References Cited

U.S. PATENT DOCUMENTS

| | | | | |
|---|---|---|---|---|
| 1,351,395 | A * | 8/1920 | Martineau | 244/135 R |
| 2,173,065 | A * | 9/1939 | Lee | 152/342.1 |
| 2,216,368 | A * | 10/1940 | Hollingshead | 152/342.1 |
| 2,650,592 | A * | 9/1953 | Borda | 604/103.02 |
| 4,085,865 | A * | 4/1978 | Thompson et al. | 222/1 |
| 4,847,203 | A | 7/1989 | Smart | |
| 5,133,084 | A * | 7/1992 | Martin | 2/468 |
| 6,071,005 | A * | 6/2000 | Ekambaram et al. | 366/173.2 |
| 6,432,698 | B1 | 8/2002 | Gaugler et al. | |

FOREIGN PATENT DOCUMENTS

| | | |
|---|---|---|
| DE | 10323315 A1 | 12/2004 |
| EP | 0343885 A1 | 11/1989 |
| GB | 2202549 A | 9/1988 |
| WO | 2005118771 A2 | 12/2005 |

* cited by examiner

*Primary Examiner* — David Sorkin

(57) ABSTRACT

The present invention is concerned with a fluid circulation apparatus for use as a bioreactor or the like, the apparatus comprising a flexible bag like container within which is disposed a collapsible and at least partially inflatable draft tube which is tethered to a base of the container such that when inflated the draft tube rises off the base and maintains the correct shape as a result of the inflation thereof, and which includes perforations in order to allow the inflation gas to escape and rise upwardly through the draft tube to generate counter current circulation within the container.

16 Claims, 4 Drawing Sheets

AIRLIFT BIOREACTOR

CROSS-REFERENCE TO RELATED APPLICATION

To the fullest extent permitted by law, the present U.S. Non-Provisional Patent Application is a U.S. National Phase Filing of and with priority to Patent Cooperation Treaty Application No. PCT/EP2007/005752, entitled "Liquid Circulation System Comprising an Inflatable Guide," filed on behalf of inventor Oliver Muecke and applicant Celljet Biotech Limited on Jul. 31, 2007, which claims priority to and the benefit of U.S. Provisional patent application entitled "Liquid Circulation System Comprising an Inflatable Guide," filed on behalf of inventor Oliver Muecke and applicant Celljet Biotech Limited, on Aug. 1, 2006, and having assigned Ser. No. 60/821,024, and which also claims priority to and the benefit of Ireland application entitled "Liquid Circulation System Comprising an Inflatable Guide," filed on behalf of inventor Oliver Muecke and applicant Celljet Biotech Limited, on Aug. 1, 2006, and having assigned No. S2005/0571.

FIELD

The present invention provides a liquid circulation apparatus for continuously mixing a liquid, and a method of mixing such a liquid. More particularly, the invention provides an apparatus for use as an airlift bioreactor for culturing prokaryotic and eukaryotic organisms or cells or the like. The bioreactor can for example be used for growing eukaryotic organisms such as, but not limited to, nematodes and other worms. In a preferred embodiment, the invention provides a disposable airlift bioreactor.

BACKGROUND

The IUPAC Compendium of Chemical Terminology defines an airlift bioreactor as "a bioreactor in which the reaction medium is kept mixed and gassed by introduction of air or another gas (mixture) at the base of a column-like reactor equipped either with a draught tube or another device (e.g. external tube) by which the reactor volume is separated into a gassed and un-gassed region thus generating a vertically circulating flow." The definition refers to internal and external loop airlift bioreactors, although the present invention is concerned only with the internal-loop airlift bioreactor.

The majority of airlift bioreactors are traditionally made out of stainless steel and designed with pressure vessel criteria in mind to sustain the required steam pressure during sterilisation. The draft tube is also made in stainless steel, is cylindrically shaped and supported in a vertical position by arms connected to the inside of the bioreactor vessel. The air inlet is generally positioned just below the draft tube, so that the gas-liquid mixture rises inside the draft tube, although the opposite circulation mode is also possible when the air inlet is positioned outside the draught tube. Hence, the overall simplicity of the bioreactor and its geometrical relationship with the draft tube makes it possible to scale-up laboratory sized bioreactors without major difficulties to sizes of up to 10,000 liters.

A disposable airlift bioreactor suited to replace the traditional airlift bioreactor would be especially attractive since it could provide considerable reduction in capital investment as well as operating costs. The reason for this is the replacement of the stainless steel bioreactor vessel with a pre-sterilised plastic bioreactor container or bag which would only be used once; making the otherwise required sterilisation (e.g. steam) and cleaning process obsolete.

So far, several attempts have been made on disposable airlift bioreactors:

P. Whitney's air lift fermenter as part of Patent GB2202549 consists of a flexible daft tube connected at the top and bottom of the plastic bag whereby the air inlet is positioned below the daft tube. The problem with this approach is that suction forces within the draft tube cause it to collapse, preventing entry of subsequent air bubbles.

The invention 'Air lift fermentor formed from flexible plastic sheets' as described in patent EP0343885 uses a 'divider panel formed of plastic film' to divide the plastic bag into two regions and thus creating circulation in the bag with an air inlet device in one of the regions. In this approach there is no risk of shear forces inside the draft region causing the dividing panel to collapse since when the bag is filed, the panel is under tension and taut. To achieve this configuration, the two plastic films forming the bag need to be bigger in size than the divider film. This precondition presents difficulties during fabrication of the bag and requires additional folding to reduce the overall volume for sterilisation and shipping.

A disposable air lift bioreactor is describes as part of U.S. Pat. No. 6,432,698 whereby again a partition is used to create a draft tube. Here the partition can either be a divider inserted in the bag or can be created by fusing a short section of the two sides of the plastic bag together. This approach is suitable for bags of small volumes, but might not withstand hydrostatic pressures if applied to larger volumes.

Patent WO2005118771 titled 'Disposable bioreactor systems and methods' mentions the possibility of a divider inside the bag, more specifically 'a sheet of plastic bisecting the chamber of the bag vertically' to enable circulation with a gas inlet element. This concept however was already described in earlier patents (see above) such as EP0343885 and U.S. Pat. No. 6,432,698

In summary, the two approaches until now for a disposable airlift bioreactor have been based either on a flexible draft tube or on a divider panel. So far, both of them have not been suitable to replace the existing traditional airlift bioreactor. The draft tube in particular has represented a problem in translating the traditional airlift bioreactor to a disposable version since bags made out of plastic sheets were already used to store and transport liquids. Hence, the challenging aspect for a disposable airlift bioreactor being able to replace traditional bioreactors consists of a draft tube or other device to provide vertical circulation in the bag.

Nowadays disposable (plastic) bags are increasingly used to store and transfer solutions required for bioprocessing. The bags can be supplied pre-sterilised and their shapes and configurations vary extensively. The majority of theses bags are generally referred to as either two or three dimensional (2D & 3D), whereby a 2D bag consists of 2 sheets of plastic sealed at their perimeter while a 3D bag consists mainly of 4 sheets of plastic sealed and cut in a particular form to create a bag with 4 sides. There are of course other bags available.

It is therefore a feature of the present invention to provide a liquid circulation apparatus, and in particular a disposable airlift bioreactor which overcomes the above mentioned problems of the prior art.

SUMMARY OF THE INVENTION

According to a first aspect of the present invention there is provided a liquid circulation apparatus comprising a container; and a circulation guide disposed internally of the container such as to define a liquid circulation path within the container; wherein the circulation guide is at least partially inflatable.

Preferably, the circulation guide comprises a draught tube.

Preferably, the circulation guide is flexible.

Preferably, the inflatable part of the circulation guide is of double walled construction, defining an inflatable cavity therebetween.

Preferably, the container comprises a flexible bag.

Preferably, the circulation guide is tethered to a base of the container.

Preferably, the circulation guide is tethered to the container in a manner which allows the guide, when inflated or partially inflated, to rise into a substantially vertical position.

Preferably, the apparatus comprises at least one inflation tube extending between an exterior of the container and the circulation guide.

Preferably, the circulation guide is wholly inflatable.

Preferably, the apparatus comprises means to aerate, in use, a liquid within the container in order to generate circulation of the liquid.

Preferably, the aeration means comprises perforations in the circulation guide which permit, in use, gas to escape in order to generate circulation within the container.

Preferably, the plurality of perforations are located on an interior portion of the circulation guide, whereby the sparging of gas into the circulation guide generates circulation within the container.

Preferably, the aeration means comprises perforations in the inflation tube.

Preferably, the container comprises at least one inlet and at least one outlet.

Preferably, the container is adapted to receive monitoring devices thereabout.

Preferably, the perforations in the circulation guide and/or the inflation tube are positioned to cause fluid circulation upwardly about the circulation guide.

Preferably, the apparatus comprises a rigid housing adapted to support the container therein.

Preferably, the apparatus comprises at least one sampling port.

According to a second aspect of the present invention there is provided a method of circulating a liquid within a container having a circulation guide therein, the method comprising aerating the liquid to generate circulation of the liquid about the circulation guide; and inflating at least a part of the circulation guide in order to maintain a desired shape and/or orientation of the circulation guide.

Preferably, the method comprises, in the step of aerating the liquid, allowing the inflation gas to escape from the circulation guide in order to simultaneously inflate at least part of the circulation guide and aerate the liquid.

Preferably, the method comprises, in the step of inflating at least a part of the circulation guide, inflating the entire circulation guide.

As used herein, the term "aerate" is intended to mean to supply or charge a liquid with a gas, especially to charge with air, oxygen, carbon dioxide or the like.

BRIEF DESCRIPTION OF THE DRAWINGS

The present invention will now be described with reference to the accompanying drawings, in which.

DETAILED DESCRIPTION

Figure 1:
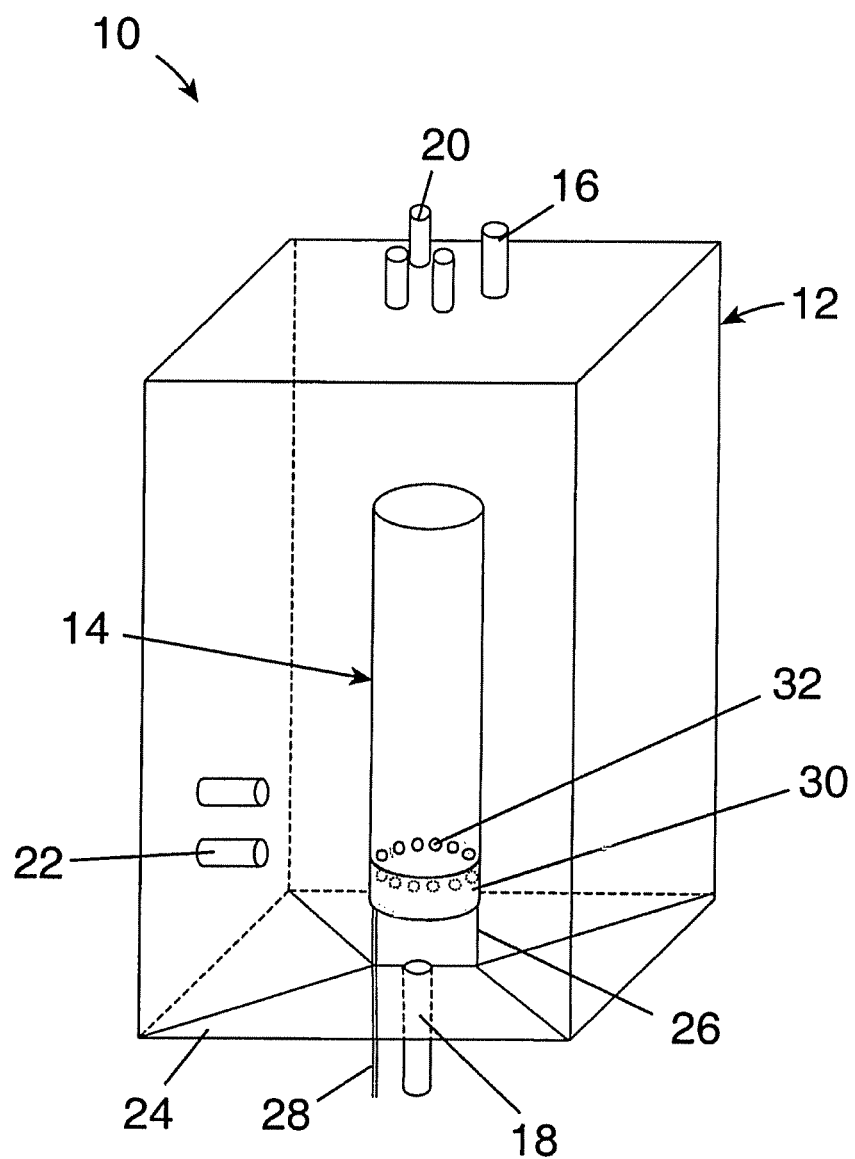
FIG. 1 illustrates a perspective schematic illustration of an airlift bioreactor according to a preferred embodiment of a liquid circulation apparatus of the present invention.
Figure 2:
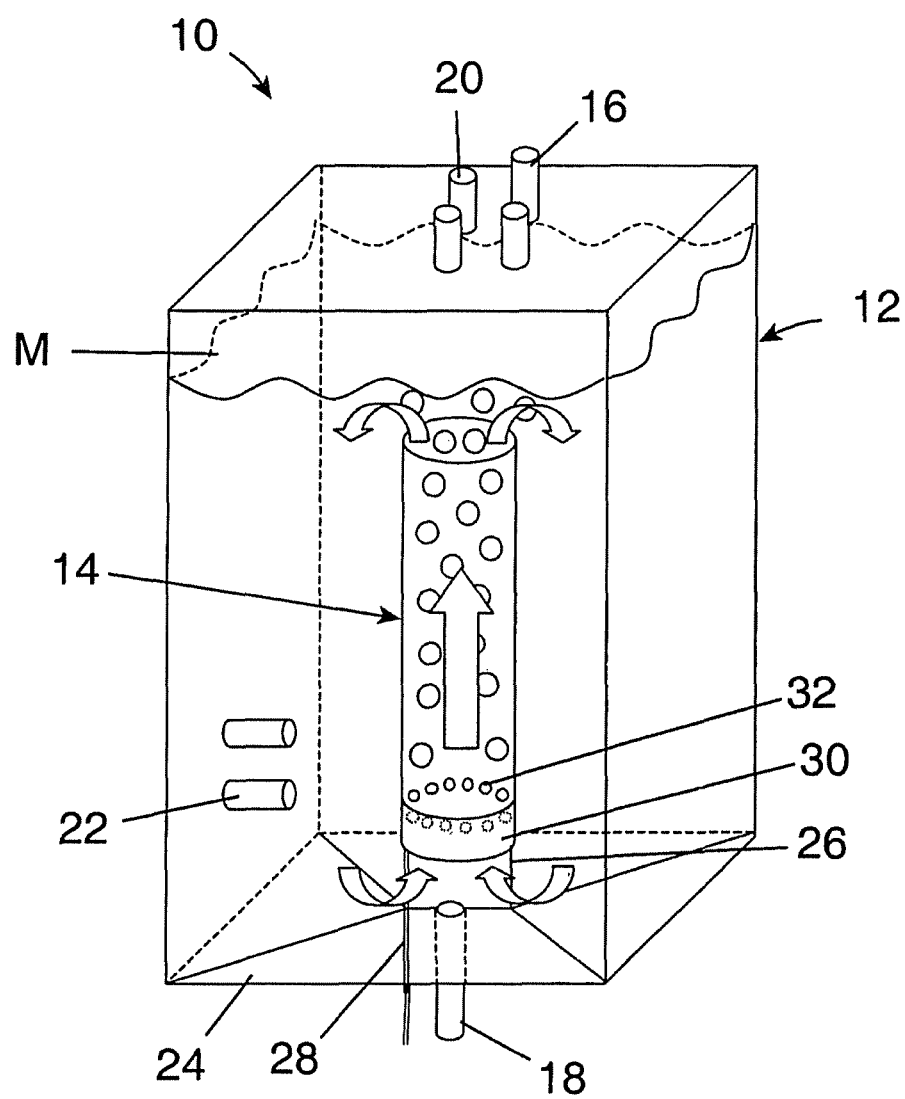
FIG. 2 illustrates the bioreactor of FIG. 1 schematically illustrating the preferred circulation of a culture medium fluid therein.

Referring now to FIGS. 1 and 2 of the accompanying drawings, there is illustrated a liquid circulation apparatus for particular application as an airlift bioreactor, generally indicated as 10, which is intended to be used in a disposable capacity, and in particular for culturing prokaryotic and eukaryotic cells or the like, in a conventional liquid based cultural medium M (not shown in FIG. 1). The bioreactor 10 comprises a container 12, which is preferably flexible and/or collapsible, such as a bag made out of plastic sheeting or the like, although in use it is likely that the container 12 will be supported within a rigid outer casing or shell or the like (not shown). The container 12 may however be formed of any other suitable material, and need not be of the shape/configuration shown. In the preferred embodiment illustrated the container 12 is formed from a sterile flexible bag where the sterility of the container may be maintained by using current techniques, e.g. filters, tube sealers & welders, asceptic connectors, etc.

Located internally of the container 12 is a liquid circulation guide in the form of a draught tube 14 which is open at either end. During normal operation of the bioreactor 10, the draught tube 14 is located in a substantially vertical orientation as illustrated, and is suspended off a base 24 of the container 12, such as to define a circulation path, most preferably a counter current vertical circulation path, for the liquid M within the container 12, as will be described in detail hereinafter.

The container 12 therefore includes one or more liquid inlet 16, preferably located at a top of the container 12, and a liquid outlet 18, preferably located at the base 24, although the location and configuration of these may be varied as required. The container 12 further comprises one or more gas exhausts 20, again preferably at a top of the container 12, in order to facilitate the venting of aeration gas introduced into the container 12 during use, again as will be described in detail hereinafter. The container 12 may also include one or more sensor receptors 22 which enable conventional monitoring devices (not shown) or similar instrumentation to be used to monitor various operating parameters of the bioreactor 10, for example the pH of the liquid culture medium M, the oxygen content, temperature, etc.

The draft tube 14 is tethered to the container 12, and in particular the base 24 thereof, by means of a support 26, although it should be understood that the tube 14 may be secured within the container 12 in any other suitable fashion. The tube 14 is further secured to the base 24 by means of an inflation tube 28 which passes from an exterior of the container 12, through the base 24, and into fluid communication with the draught tube 14. In particular, the inflation tube 28 connects with a lower annular portion 30 of the tube 14, which is inflatable, preferably by means of a double wall arrangement defining an inflatable cavity therebetween. It should however be appreciated, in particular from the following description of the operation of the bioreactor 10, that the entire draught tube 14 could be inflatable in similar fashion to the annular portion 30.

In the preferred embodiment illustrated, the bioreactor 10 is provided with aeration means in the form of perforations or sparge holes 32 located on an interior wall of the annular portion 30, in order to allow the escape of gas from the annular portion 30, to rise upwardly through the tube 14. This aeration, in use, effects circulation of the fluid M within the container 12, in particular by counter current vertical circulation upwardly and around the draft tube 14.

Thus, in use, the container 12 of the bioreactor 10 is filled with the liquid culture medium M, and provided with a quantity of cells or organisms to be cultured. The inflation tube 28 is then connected to a supply of gas, preferably air, and this gas is then pumped into at least the annular portion 30 of the draft tube 14. This results in inflation of the annular portion 30, which therefore results in the opening or unfurling of the annular portion 30 to its full cross sectional shape. This then opens up the remainder of the draught tube 14, and also results in the draught tube 14 rising into a vertical position as illustrated, due to the buoyancy of the air or other gas inflating same. The air or other gas pumped into the annular portion 30 will then begin to escape through the sparge holes 32, creating a flow of gas bubbles rising upwardly through the draught tube 14, as illustrated in FIG. 2.

This upward aeration through the draught tube 14 sets up a counter-current circulation within the container 14, as indicated by the directional arrows on FIG. 2. The upward flow of liquid through the draught tube 14 creates suction forces within the draught tube 14, which would normally act to force the draught tube 14 to at least partially collapse in oil itself, retarding or terminating the circulation through same. However, by effecting inflation of at least the annular portion 30, the inflated draught tube 14 provides stability against these suction forces, thus preventing the draught tube 14 from collapsing. The tethering of the tube 14 to the base 24 via the support 16, and to a lesser extent by the inflation tube 28, ensures that the draught tube 14 remains in the position illustrated, floating off the base 24 to facilitate the counter current circulation therethrough.

By using an inflatable draft tube 14, the draft tube 14 can be flexible, and therefore collapsible, allowing the bioreactor, when empty, to be collapsed for storage and/or transport or the like. In addition, when the bioreactor is filled with the culture medium M, the flexibility of the tube 14, and the container 12, provides a number of advantages over a rigid arrangement, which advantages are well documented with respect to other flexible vessels or bags used to store and transfer solutions required for bioprocessing, not least of which is the reduced cost of manufacture of the bioreactor 10.

As an alternative to the location of the sparge holes 32 about the annular portion 30, it is possible that the section of inflatable tube 28 between the base 24 and the annular portion 30 could itself be perforated, in order to allow the escape of gas therefrom, to flow upwardly through the draught tube 14. It should also be appreciated that the draught tube 14 need not be circular in cross-section, as illustrated, and could be of any other suitable shape or configuration.

The bioreactor 10 can also be used as processing equipment for the manufacture of plasmid DNA. Plasmid DNA is used in the pharmaceutical industry for gene therapy products and needs to be prepared and isolated after fermentation of the bacterial cells. Chemical lysis of the cells results in disintegration of the cells and precipitation of chromosomal DNA, while the plasmid DNA remains in solution. The bioreactor 10 could therefore be provided with an additional port (not shown) next to the liquid outlet 18, but extended to reach into the draft tube 14, via which the chemical lysis gas/solution can be introduced into the bioreactor 10 in a continuous manner during mixing.

Figure 3:
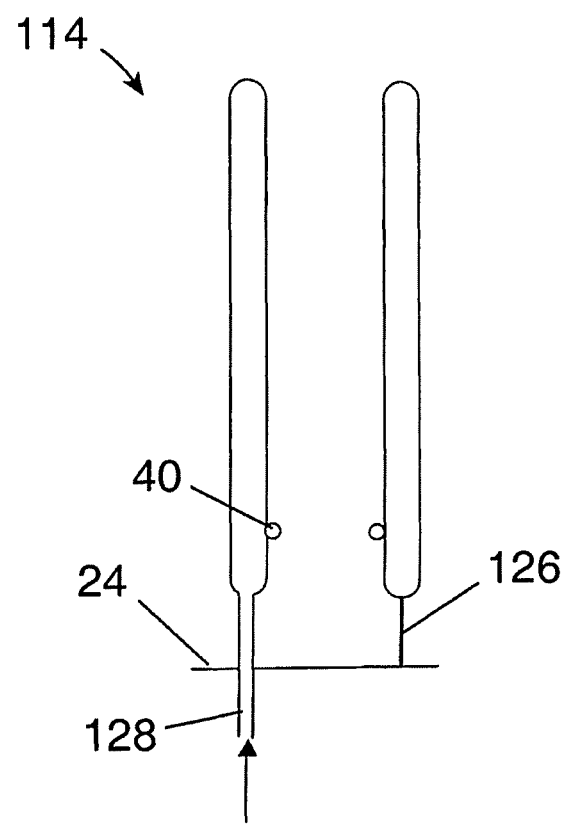
FIG. 3 illustrates a sectioned side elevation of a draught tube forming part of the bioreactor of FIGS. 1 and 2.
Figure 4:
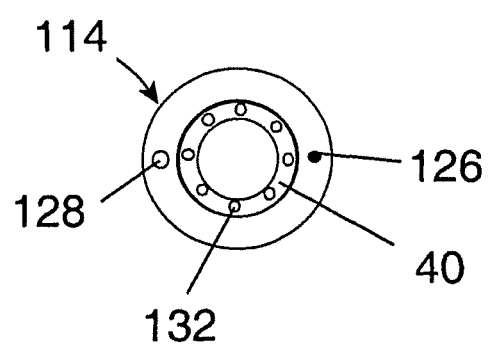
FIG. 4 illustrates a plan view of the draft tube illustrated in FIG. 3.

Referring now to FIGS. 3 and 4, there is illustrated an alternative embodiment of a draught tube, generally indicated as 114, for use with the bioreactor 10 of the present invention. The draught tube 114 is tethered to the base 24 of the container, via a support 126. Again, an inflation tube 128 passes from an exterior of the container into fluid communication with the draught tube 114, which is inflatable along the full length thereof, and which is again of double wall configuration in order to allow the inflation thereof. The draught tube 114 includes an inner circumferential ring 40 which is also inflatable, and on an upper face of which is provided an array of sparge holes 132. The sparge holes 132 permit the escape of the inflation gas from the draught tube 114, in order to effect the vertical aeration of the draught tube 114, thereby generating fluid circulation upwardly through the draft tube 114.

Figure 5:
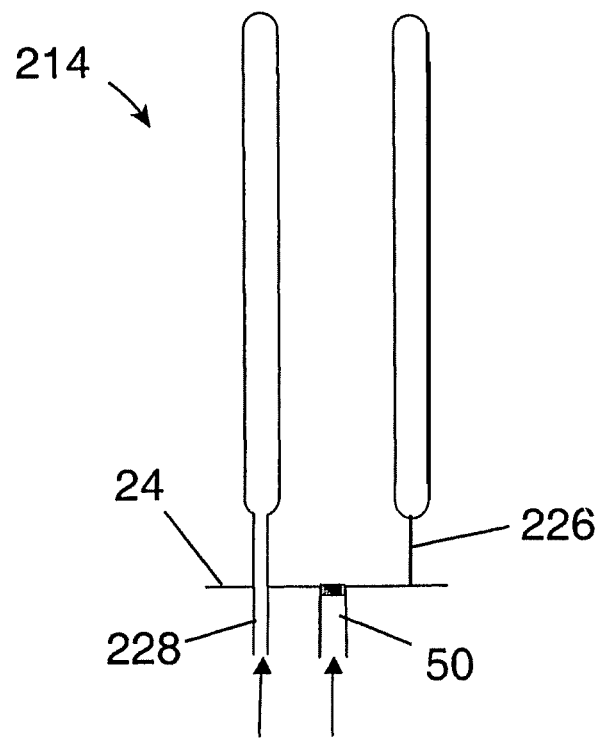
FIG. 5 illustrates a sectioned side elevation of an alternative draught tube for use with the bioreactor of FIGS. 1 and 2.
Figure 6:
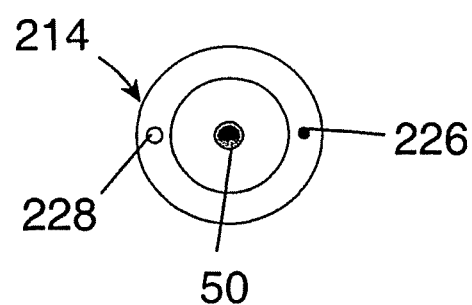
FIG. 6 illustrates a plan view of the draught tube illustrated in FIG. 5.

Referring then to FIGS. 4 and 5, there is illustrated a further alternative embodiment of a draught tube, generally indicated as 214, for use with the bioreactor 10 of the present invention. The draught tube 214 is again tethered to the base 24 via a support 226. An inflation tube 228 extends from an exterior of the container into fluid communication with the draught tube 214. However, unlike the draught tube 14 illustrated in FIGS. 1 and 2, the draught tube 214 does not include any perforations therein, or any other means to allow the escape of the inflation gas therefrom. Thus, in order to effect aerated counter current vertical circulation through the draught tube 214, a sparge tube 50 is provided, which opens onto the interior of the base 24, and through which may be supplied gas, in particular air, in order to effect the upward aeration of the draught tube 214.

In an alternative embodiment (not shown) of the present invention, a plurality of circulation guides may be provided in a single container. The circulation guides may be placed side by side, stacked one on top of the other, or positioned in any other suitable or desired formation. Each circulation guide may be supplied with gas from an inflation tube. In this manner, the aspect ratio of the container may be adjusted as desired to achieve the desired level of mixing, while achieving a desired size and shape of the container.

It will therefore be appreciated that the bioreactor 10, and in particular the flexible and inflatable/collapsible nature of the draft tube 14; 114; 214, enables the entire bioreactor 10 to be provided as a flexible/collapsible unit with significant reductions in cost of manufacture and operation. The operation of the bioreactor 10 of the invention is further improved and refined by combining the use of a gas to both inflate the draft tube 14 and to effect aeration of the circulation medium M. The bioreactor 10 therefore extracts a dual functionality from the gas supplied thereto.

The invention claimed is:

1. A liquid circulation bioreactor apparatus comprising a container; and a circulation guide comprising a draft tube open at both ends thereof and tethered to a base of the container in a manner which allows the draft tube, when inflated or partially inflated, to rise into a substantially vertical position; and disposed entirely internally of the container such as to define a vertical counter current liquid circulation path within the container, wherein the circulation guide is at least partially gas inflatable.

2. A liquid circulation apparatus according to claim 1, wherein the circulation guide is flexible.

3. A liquid circulation apparatus according to claim 1, wherein the inflatable part of the circulation guide is of double walled construction, defining an inflatable cavity therebetween.

4. A liquid circulation apparatus according to claim 1, wherein the container comprises a flexible bag.

5. A liquid circulation apparatus according to claim 1, comprising at least one inflation tube extending between an exterior of the container and the circulation guide.

6. A liquid circulation apparatus according to claim 1, wherein the circulation guide is wholly inflatable.

7. A liquid circulation apparatus according to claim 1, comprising means to aerate, in use, a liquid within the container in order to generate circulation of the liquid.

8. A liquid circulation apparatus according to claim 7, wherein the aeration means comprises perforations in the circulation guide which permit, in use, gas to escape in order to generate circulation within the container.

9. A liquid circulation apparatus according to claim 8, wherein the plurality of perforations are located on an interior portion of the circulation guide, whereby the sparging of gas into the circulation guide generates circulation within the container.

10. A liquid circulation apparatus according to claim 7, wherein said means to aerate comprises perforations in an inflation tube.

11. A liquid circulation apparatus according to claim 1, wherein the container comprises at least one inlet and at least one outlet.

12. A liquid circulation apparatus according to claim 1, wherein the container is adapted to receive monitoring devices thereabout.

13. A liquid circulation apparatus according to claim 8, wherein the perforations in the circulation guide and/or an inflation tube are positioned to cause fluid circulation upwardly about the circulation guide.

14. A liquid circulation apparatus according to claim 1 comprising a rigid housing adapted to support the container therein.

15. A liquid circulation apparatus according to claim 1 comprising at least one sampling port.

16. A liquid circulation bioreactor apparatus comprising a container; and a circulation guide comprising a draft tube open at both ends thereof and tethered to a base of the container in a manner which allows the draft tube, when inflated or partially inflated, to rise into a substantially vertical position; wherein said draft tube is disposed entirely internally of the container such as to define a vertical counter current liquid circulation path within the draft tube and the container, wherein said liquid circulation path travels through said both ends of said draft tube; wherein the circulation guide is at least partially gas inflatable.

* * * * *